(12) United States Patent
Charles (10) Patent No.: US 11,045,089 B2
(45) Date of Patent: Jun. 29, 2021

(54) AUTOMATIC LENS TO CORNEA STANDOFF CONTROL FOR NON-CONTACT VISUALIZATION

(71) Applicant: Novartis AG, Basel (CH)

(72) Inventor: Steven T. Charles, Germantown, TN (US)

(73) Assignee: Alcon Inc., Fribourg (CH)

( * ) Notice: Subject to any disclaimer, the term of this patent is extended or adjusted under 35 U.S.C. 154(b) by 63 days.

(21) Appl. No.: 15/979,798

(22) Filed: May 15, 2018

(65) Prior Publication Data

US 2018/0333049 A1 Nov. 22, 2018

Related U.S. Application Data

(60) Provisional application No. 62/508,617, filed on May 19, 2017.

(51) Int. Cl.

| | | |
|---|---|---|
| *G02B 21/00* | (2006.01) | |
| *A61B 3/13* | (2006.01) | |
| *A61B 3/00* | (2006.01) | |
| *A61B 90/50* | (2016.01) | |
| *G02B 21/24* | (2006.01) | |
| *A61B 90/25* | (2016.01) | |
| *A61B 3/14* | (2006.01) | |

(52) U.S. Cl.
CPC .............. *A61B 3/13* (2013.01); *A61B 3/0075* (2013.01); *A61B 3/14* (2013.01); *A61B 90/25* (2016.02); *A61B 90/50* (2016.02); *G02B 21/0012* (2013.01); *G02B 21/241* (2013.01)

(58) Field of Classification Search
CPC .......................... G02B 21/00; G02B 21/0012; G02B 21/0016; G02B 21/0028; G02B 21/006; G02B 21/24; G02B 21/241; G02B 21/244; A61B 3/0075; A61B 3/13; A61B 3/14; A61B 90/25; A61B 90/50
USPC .......................................... 359/368, 379–383
See application file for complete search history.

(56) References Cited

U.S. PATENT DOCUMENTS

| | | | | |
|---|---|---|---|---|
| 6,980,359 | B2 * | 12/2005 | Yoneyama | G02B 21/24 |
| | | | | 359/368 |
| 7,130,117 | B2 * | 10/2006 | Tsuyuki | G02B 7/08 |
| | | | | 359/383 |
| 7,901,080 | B2 * | 3/2011 | Hauger | A61B 3/13 |
| | | | | 351/246 |
| 7,940,455 | B2 * | 5/2011 | Gaida | A61B 3/13 |
| | | | | 359/379 |
| 9,259,149 | B2 | 2/2016 | Holladay | |
| 9,693,686 | B2 | 7/2017 | Smith | |
| 9,877,648 | B2 | 1/2018 | Farley | |
| 2002/0191280 | A1 | 12/2002 | Horiguchi | |

(Continued)

*Primary Examiner* — Thong Q Nguyen (57) ABSTRACT

Systems, methods, and computer-readable media for automatically controlling a lens to cornea standoff. Automatic lens to cornea standoff control can include an ophthalmic microscope with a lens arrangement configured for viewing images of an eye, a front lens assembly with a high diopter lens for resolving an image of a posterior portion of the eye, and a sensor to monitor a distance between the high diopter lens and a surface of the eye. Automatic lens to cornea standoff control can also include a control system for receiving distance information and an actuator for the front lens assembly back to the threshold standoff distance, past the threshold standoff distance, etc.

20 Claims, 10 Drawing Sheets

(56) References Cited

U.S. PATENT DOCUMENTS

| | | | |
|---|---|---|---|
| 2002/0198516 A1* | 12/2002 | Knopp | A61F 9/00804 606/5 |
| 2004/0183999 A1 | 9/2004 | Kogawa | |
| 2013/0113919 A1* | 5/2013 | Qiao | G01B 11/026 348/92 |
| 2013/0338649 A1* | 12/2013 | Hanebuchi | A61F 9/0084 606/4 |
| 2015/0002808 A1* | 1/2015 | Rizzo, III | G02C 11/10 351/158 |
| 2015/0335479 A1* | 11/2015 | Shibata | A61F 9/009 606/5 |
| 2016/0106581 A1* | 4/2016 | Gonzalez | A61F 9/009 128/845 |
| 2016/0353990 A1* | 12/2016 | Smith | A61B 3/13 |
| 2017/0045721 A1 | 2/2017 | Charles | |
| 2017/0281404 A1* | 10/2017 | Wang | A61F 9/009 |
| 2018/0000641 A1* | 1/2018 | Rathjen | A61F 9/008 |
| 2020/0178795 A1* | 6/2020 | Ishikawa | A61B 3/13 |

\* cited by examiner

AUTOMATIC LENS TO CORNEA STANDOFF CONTROL FOR NON-CONTACT VISUALIZATION

BACKGROUND

Field of the Disclosure

The present disclosure relates to ophthalmic surgery, and more specifically, to an automatic lens standoff system for use during ophthalmic surgery.

Description of Related Art

Ophthalmic surgery is commonly performed using an operating microscope to visualize various structures in the eye. For example, during cataract surgery, the microscope if used to visualize the anterior segment of the eye such as the cornea, lens, etc. However, a standard operating microscope does not adequately view an entire posterior segment (e.g. the retina) of the eye because the natural optics of the eye (e.g. the cornea and the lens) prevent the operating microscope from focusing on features of the posterior of the eye.

To achieve superior posterior viewing during retinal surgery, an operating microscope can be used in conjunction with an additional optical system that is capable of resolving an image of the retina of the eye. For example, an ophthalmoscopic contact lens can contain an optical system for wide-angle viewing of the retina and can be placed over a patient's eye. The operating microscope can then be focused to view an image created by the contact lens. However, a contact lens system can interfere with a surgeon's ability to manipulate surgical instruments. Also, the ophthalmoscopic contact lens can become misaligned as a result of movements by the patient.

A front lens assembly can also be used in conjunction with an operating microscope to achieve wide angle viewing of the retina or viewing of the macula. A front lens assembly can include a supportive member that can hold a contact-less front lens above the eye of the patient. However, during the course of ophthalmic surgery, liquids from the eye and/or liquids used to wet the cornea can obscure a front lens when it inadvertently contacts the cornea, requiring the surgeon to clean the lens or to replace the lens.

Cleaning an ophthalmoscopic contact lens and/or a front lens can be troublesome for a number of reasons. The process of cleaning the lenses can take time away from performing the surgery and cause less desirable outcomes. Also, the ophthalmoscopic contact lens and/or a front lens can have surface features (e.g. diffractive surface features) that make effective cleaning very difficult. As an alternative to cleaning a front lens, a retinal surgeon oftentimes elects to replace the front lens with a lens from a reserve of replacement lenses to ensure continuity during surgery. However, typical lens used for wide angle retinal viewing are diamond turned glass and are very expensive.

SUMMARY

The disclosed embodiments of the present technology relate to systems, methods, and computer-readable media for automatically controlling a lens to cornea standoff. A system for automatic lens to cornea standoff control can include an ophthalmic microscope with a lens arrangement configured for viewing images of an eye and a front lens assembly with a high diopter lens for resolving an image of a posterior portion of the eye. The front lens assembly can adjustably position the high diopter lens at various positions between the lens arrangement of the ophthalmic microscope and the eye. In some cases, the front lens assembly includes a multi-sectional articulating arm for adjustably positioning the high diopter lens. The front lens assembly can also be a screw drive system for to adjustably positioning the high diopter lens.

The system can also include a sensor that can monitor a distance between the high diopter lens and a surface of the eye. The sensor can be an ultrasonic sensor, a laser triangulation sensor, an infrared sensor, etc. In some cases, the sensor is coupled with the lens holder of the front lens assembly.

The sensor is communicatively coupled with a control system for receiving information from the sensor describing the distance between the high diopter lens and a surface of the eye. In some cases, the sensor is wirelessly coupled with the control system. The control system is further configured to receive the detected distance from the sensor and determine when the detected distance is less than a predetermined threshold standoff distance.

When the detected distance is less than a predetermined threshold standoff distance, the control system can cause an actuator coupled with the front lens assembly to move the front lens assembly back to the threshold standoff distance, past the threshold standoff distance, etc. In some cases, when the controller can also enforce a second predetermined threshold standoff distance to keep the high diopter lens within a range (e.g. 5-10 millimeters) of distances away from an eye surface.

The system can also include an auto-focus system coupled with the controller. The auto-focus system can automatically focus the lens arrangement of the ophthalmic microscope to resolve an image of the eye that was being resolved before a position of the high diopter lens was moved by the movement of the front lens assembly.

The system can also include a user interface for receiving a user-defined standoff preference, surgical data, or an over-ride signal that can prevent or throttle a control signal for moving the front lens assembly.

Methods of maintaining a lens to cornea standoff can involve a sensor monitoring a distance between a corneal surface of an eye and a high diopter lens in a front lens assembly and a control system receiving, from the sensor, the distance measurement. Some methods also include the control system comparing the distance measurement to a predetermined threshold standoff distance and transmitting a control signal to an actuator when the distance measurement is less and the predetermined threshold standoff distance.

In some cases, method of maintaining a lens to cornea standoff can involve the actuator receiving a control signal and moving the front lens assembly to position the high diopter lens at the threshold distance, past the threshold distance, etc. Some methods also involve the control system transmitting an instruction to an autofocus system to focus the lens arrangement in order to resolve an image of the eye that was being resolved before a position of the high diopter lens was moved.

BRIEF DESCRIPTION OF THE DRAWINGS

For a more complete understanding of the present technology, its features, and its advantages, reference is made to the following description, taken in conjunction with the accompanying drawings, in which.

DESCRIPTION

As explained above, a front lens assembly can be used in conjunction with an operating microscope to achieve wide angle viewing of the retina or viewing of the macula. In general, the closer the front lens is to the eye the greater the field of view for clear visualization of the peripheral retina and to repair retinal tears and retinal detachments. The disclosed technology involves encouraging high field of view by maintaining a close distance between a front lens and a patient's cornea while preventing corneal-front lens contact resulting in view morphing viscoelastic material on the lens surface and corneal epithelial damage.

Figure 1:
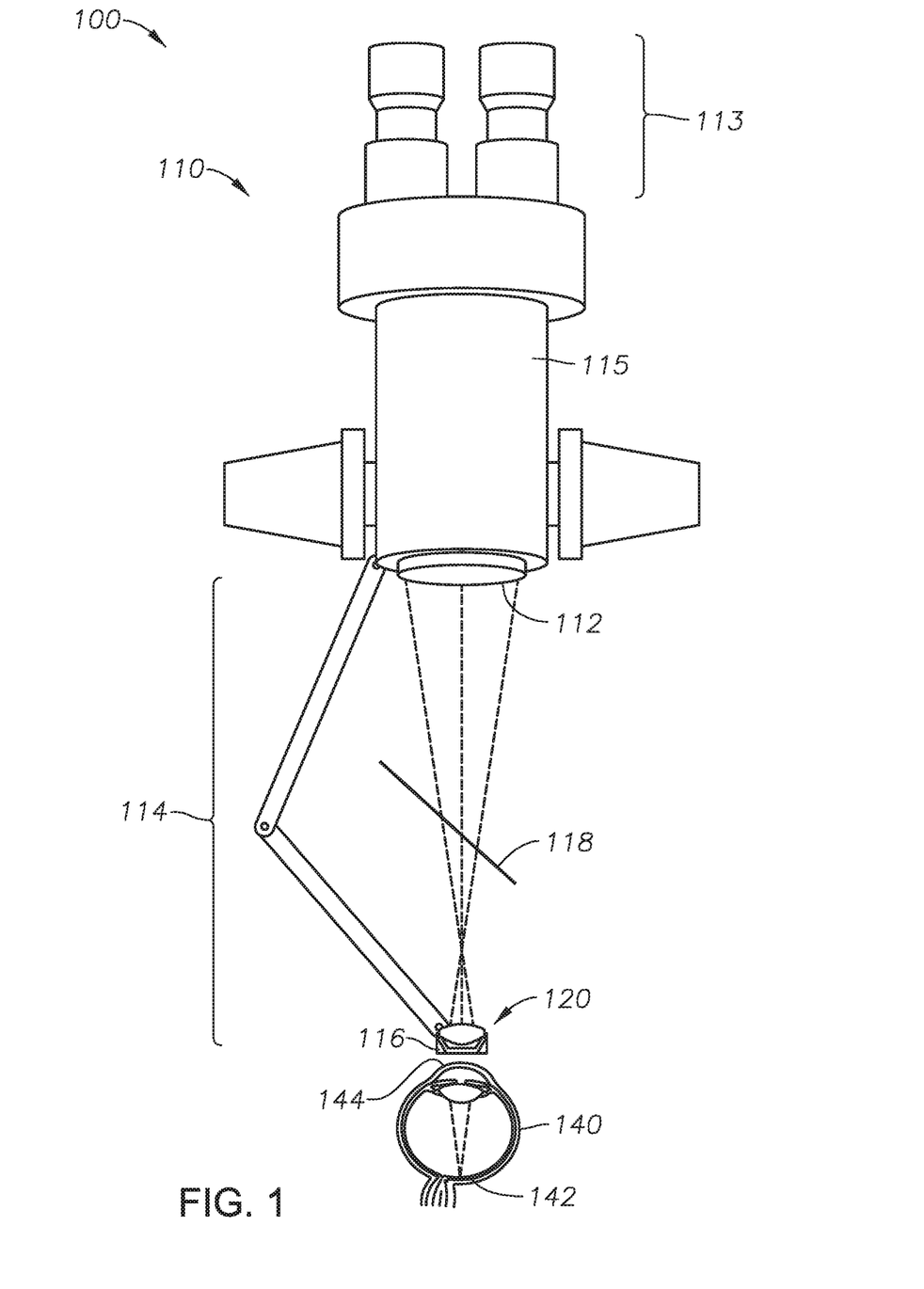
FIG. 1 illustrates a system for high resolution, wide field of view viewing of the retina of an eye.

Systems and methods are disclosed for providing automatic lens to cornea standoff in an ophthalmic surgery system. FIG. 1 illustrates a system 100 for high resolution, wide field of view viewing of the retina 142 of an eye 140. The system 100 can include a high diopter lens 120 used in conjunction with an ophthalmic microscope 110. The ophthalmic microscope 110 can include a housing 115 containing a lens arrangement including an objective lens 112. The ophthalmic microscope 110 also includes a binocular eyepiece arrangement 113 for viewing images formed from a beam of light reflected from the eye 140. The system 100 can also include a beamsplitter 118 to redirect a portion of the beam of light.

The system 100 can also include a front lens assembly 114 coupled with the ophthalmic microscope 110. The front lens assembly can include a lens holder 116 for supporting the high diopter lens 120. In some cases, the front lens assembly 114 can be jointed and can articulate in order to alternatively raise and lower the lens holder 116 and high diopter lens 120 and/or position the lens holder 116 and the high diopter lens into and out of the beam of light. In some cases, the front lens assembly 114 is configured as a screw drive that can move the lens holder 116 up and down and the lens holder 116 and that can rotate lens holder 116 into and out of the beam of light. Also, although jointed and screw drive configurations are explicitly mentioned herein, those with ordinary skill in the art having the benefit of the present disclosure will readily appreciate that a wide variety of positioning systems can be used in a front lens assembly to achieve the benefits of the disclosed technology.

In some cases, the lens arrangement of the ophthalmic microscope 110 is generally selected to resolve an image of the anterior (e.g. a cornea 144) of an eye. Similarly, the prescription of the high diopter lens 120 can selected to resolve an image of the retina 142 of the eye 140 when used in combination with the lens arrangement of the ophthalmic microscope 110. In these cases, an ophthalmic professional can alternatively view the anterior and retina 142 of the eye 140 by articulating the lens holder 116 and the high diopter lens into and out of the beam of light.

As explained above, during the course of ophthalmic surgery, fluids from the eye and/or fluids used to wet the cornea can obscure a front lens when the front lens makes contact with the cornea, requiring the surgeon to clean the lens or to replace the lens. Therefore, to avoid the patient's eye becoming too close or even contacting the high diopter lens 120, surgeons routinely position the front lens assembly 114 to place the high diopter lens 120 at a standoff distance away from the patient's eye. However, the position of patient's eye may move during the course of a surgery. For example, during an ophthalmic surgery, patients oftentimes move their heads up and down with respiratory movements. With these movements, the standoff distance can be impinged and fluids can come in contact with the high diopter lens 120.

Accordingly, a system 100 for high resolution, wide field of view viewing of the retina 142 of an eye 140 can include one or more sensor for sensing the distance from the high diopter lens 120 and the cornea 144 of the eye 140.

Figure 2:
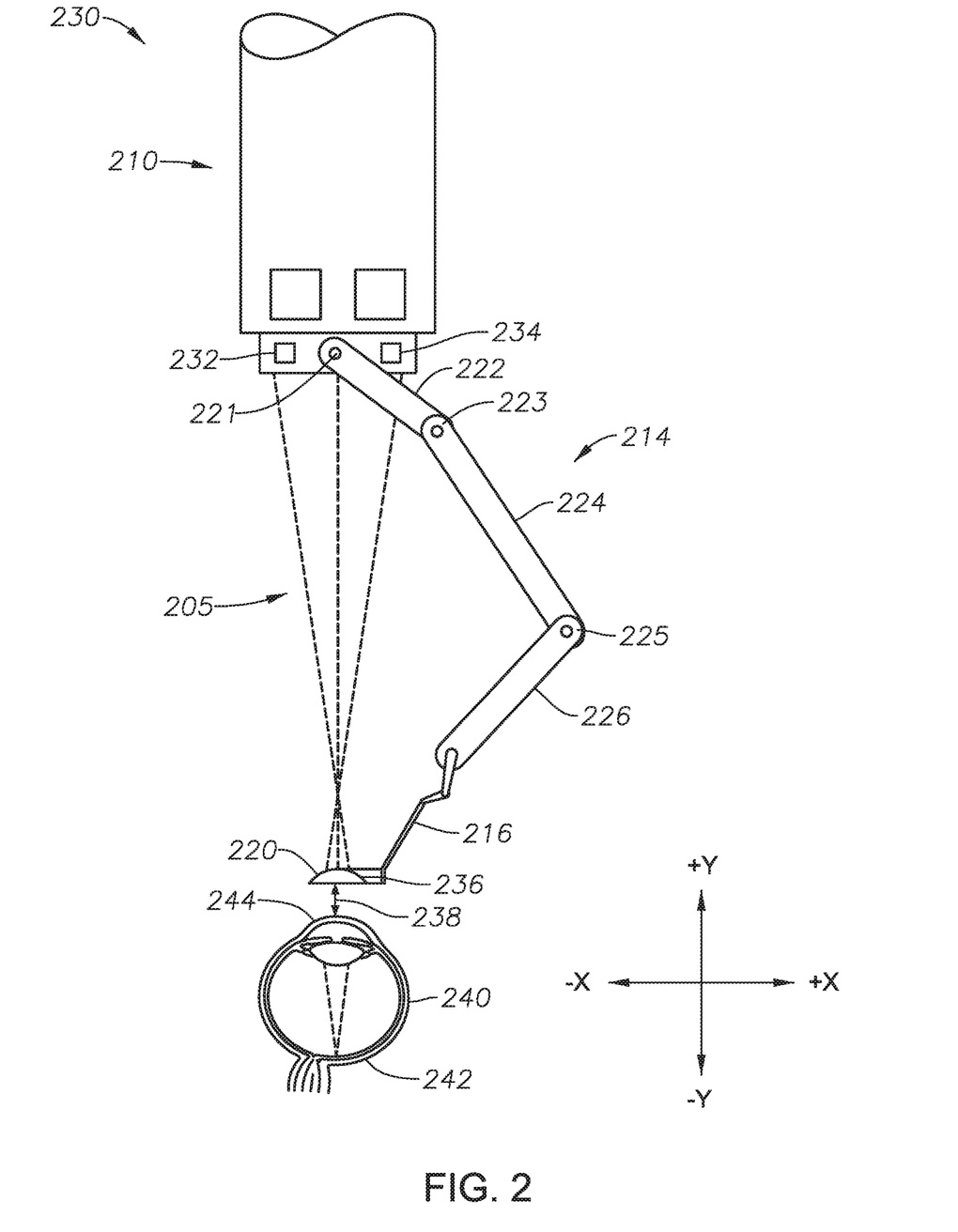
FIG. 2 illustrates an automatic lens to cornea standoff system.

FIG. 2 illustrates an automatic lens to cornea standoff system 230 according to some embodiments of the present technology. The automatic lens to cornea standoff system 230 can include a front lens assembly 214 coupled to an ophthalmic microscope 210. The front lens assembly 214 includes a lens holder 216 supporting a high diopter lens 220 between a lens arrangement (not shown) of the ophthalmic microscope 210 and an eye 240. Also, the front lens assembly 214 is configured to adjustably position the high diopter lens 220 at a plurality of positions between the lens assembly and the eye 240. As shown in FIG. 2, the front lens assembly 214 is a multi-sectional articulating arm assembly with a first articulating section 222 that can rotate in the X-Y plane about a first joint 221 coupled with the ophthalmic microscope 210. The multi-sectional front lens assembly 214 also includes a second articulating section 224 and a third articulating section 226 which are able to rotate in the X-Y plane about the second joint 223 and the third joint 225, respectively. The multi-sectional front lens assembly 214 shown in FIG. 2 allows the high diopter lens 220 to be adjustably positioned in a variety of positions between the lens arrangement and the eye 240 while still remaining co-axial with a beampath 205 of the lens arrangement.

The automatic lens to cornea standoff system 230 also includes a sensor 236 coupled with the lens holder 216. The sensor 236 can detect a distance between the sensor 236 and a surface (i.e. a corneal surface 244) of the eye 240. The bottom surface of the sensor 236 can substantially aligned with the bottom of the high diopter lens 220 and/or a difference between the bottom surface of the sensor 236 and bottom of the high diopter lens 220 is known to a controller. Accordingly, the sensor 236 (along with the controller) can also determine a distance 238 between the high diopter lens 220 and the surface of the eye 240.

The sensor 236 is communicatively coupled with a controller 232, as explained in greater detail below. Also, the controller 232 can include memory for storing threshold standoff distances, e.g. default values, user-defined standoff value preferences, etc. Furthermore, the controller 232 can receive a detected distance 238 from the sensor 232 and determine that the detected distance 238 is greater or less than the predetermined threshold standoff distance, e.g. when a patient moves his head during surgery.

The automatic lens to cornea standoff system 230 also includes an actuator 234 coupled with the controller 232 and the front lens assembly 214. In some cases, the first joint 221, the second joint 223, and the third joint 225 also include actuators for causing the articulating sections 222, 224, 226 to rotate. For ease of explanation, the disclosure refers to the actuator 234 controlling the articulating sections; however, any of the actuators in the joints or actuators located elsewhere in the automatic lens to cornea standoff system 230 can receive control instructions and cause the front lens assembly to articulate.

After the controller 232 determines that the detected distance 238 is less than a first predetermined threshold standoff distance, the controller 232 can send a control signal to the actuator 234. The control signal can cause the actuator 234 to move the front lens assembly 214 and can cause the high diopter lens 220 to move a distance away from the corneal surface 244, i.e. past the threshold standoff distance. For example, the actuator 234 can cause the first articulating section 222 to rotate up (i.e. in the +y direction) about the first joint 223, can cause the second articulating section 224 to rotate towards the beampath 205 (i.e. in the −x direction) and can cause the third articulating section 226 to rotate up (i.e. in the +y direction) about the third joint 225, thereby keeping the high diopter lens 220 co-axial with the beampath 205. In some cases, the actuator 234 can further cause that lens holder 216 to rotate to further keep the high diopter lens 220 co-axial with the beampath 205.

In some cases, when the controller 232 determines that the detected distance 238 is greater than a second predetermined threshold standoff distance, the controller 232 can send a control signal to the actuator 234, causing the actuator 234 to move the front lens assembly 214 and can cause the high diopter lens 220 toward the corneal surface 244.

The standoff distance thresholds can cause the controller to keep the high diopter lens within a range of distances away from an eye surface. For example, the standoff distance thresholds can maintain a 5-10 millimeter distance between the high diopter lens and the eye.

Figure 3:
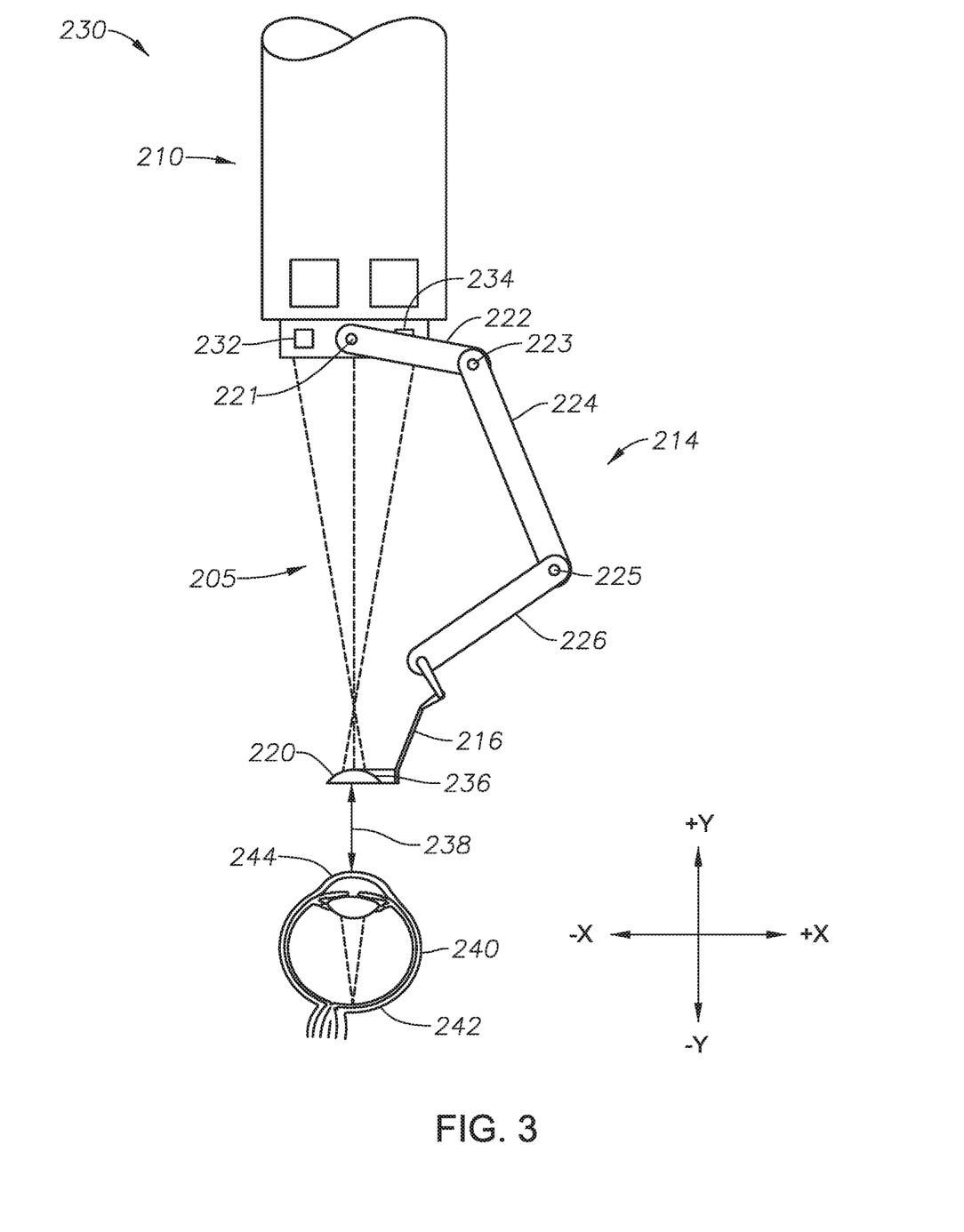
FIG. 3 illustrates the automatic lens to cornea standoff system after the high diopter lens is moved away from the corneal surface.

FIG. 3 illustrates the automatic lens to cornea standoff system 230 after the actuator 234 moves the front lens assembly 214 and causes the high diopter lens 220 to move a distance away from the corneal surface 244. As shown, the detected distance 238 of FIG. 3 is larger than the detected distance 238 of FIG. 2 after the actuator 234 moved the high diopter lens 220. Further, the high diopter lens 220 remains co-axial with the beampath 205, thereby still allowing surgical staff to view an image of a posterior portion of the eye 240 (e.g. a retina 242). In some cases, the actuator 234 can further cause that lens holder 216 to rotate to further co-axially align the high diopter lens 220.

While a standoff distance between the high diopter lens 220 and a surface of the eye is maintained by the actuator 234 moving the front lens assembly 214, a distance between an objective lens (not shown) of the lens arrangement of the ophthalmic microscope 210 is changed. Therefore, in some cases, the controller 232 includes and/or is coupled to an autofocus system (explained in greater detail below) for automatically adjusting the lens arrangement for resolving a target image, e.g. the retina 242.

Figure 4:
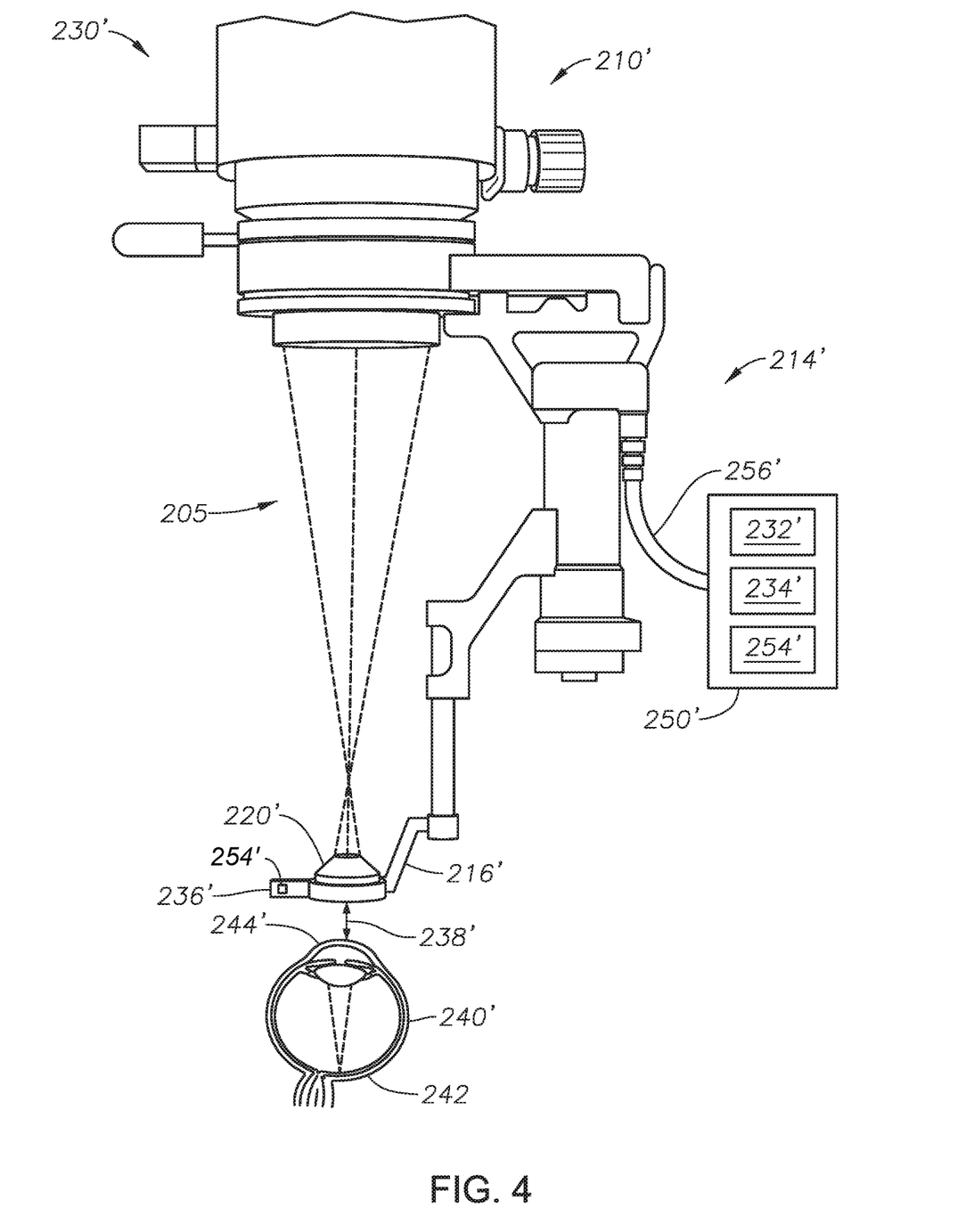
FIG. 4 illustrates an automatic lens to cornea standoff system with a screw drive front lens assembly.

FIG. 4 illustrates an automatic lens to cornea standoff system 230' with a screw drive front lens assembly 214' according to some embodiments of the present technology. The screw drive a front lens assembly 214' is coupled to an ophthalmic microscope 210' and includes a lens holder 216' supporting a high diopter lens 220' between a lens arrangement (not shown) of the ophthalmic microscope 210' and an eye 240'. The screw drive front lens assembly 214' contains a motor (not shown) configured to adjustably position the high diopter lens 220' at a plurality of positions between the lens assembly and the eye 240'.

The automatic lens to cornea standoff system 230' also includes a sensor 236' coupled with the lens holder 216'. The sensor 236' can detect a distance between the sensor 236' and a surface (i.e. a corneal surface 244') of the eye 240'. Accordingly, the sensor 236' (along with the controller) can also determine a distance 238' between the high diopter lens 220' and the surface of the eye 240'.

The motor in the screw drive front lens assembly 214' of the automatic lens to cornea standoff system 230' can be connected to a control system 250', e.g. via a wired connection 256'. The control system 250' can include a controller 232' communicatively coupled with the sensor 236'. In some cases, the controller 232' is coupled with a wireless interface which can wirelessly communicate with a wireless interface 254' in the sensor 236'.

Also, the controller 232' can include memory for storing a threshold standoff distance, e.g. a default value, a user-defined standoff value preference, etc. Furthermore, the controller 232' can receive a detected distance 238' from the sensor 236' and determine that the detected distance 238' is less than the predetermined threshold standoff distance, e.g. when a patient moves his head during surgery.

The control system 250' can also include an actuator 234' coupled with the motor in the screw drive front lens assembly 214'. After the controller 232' determines that the detected distance 238' is less than the predetermined threshold standoff distance, the controller 232' can send a control signal to the actuator 234'. The control signal can cause the actuator 234' to drive the motor in the screw drive front lens assembly 214' and can cause the high diopter lens 220' to move a distance away from the corneal surface 244', i.e. past the threshold standoff distance.

Figure 5A:
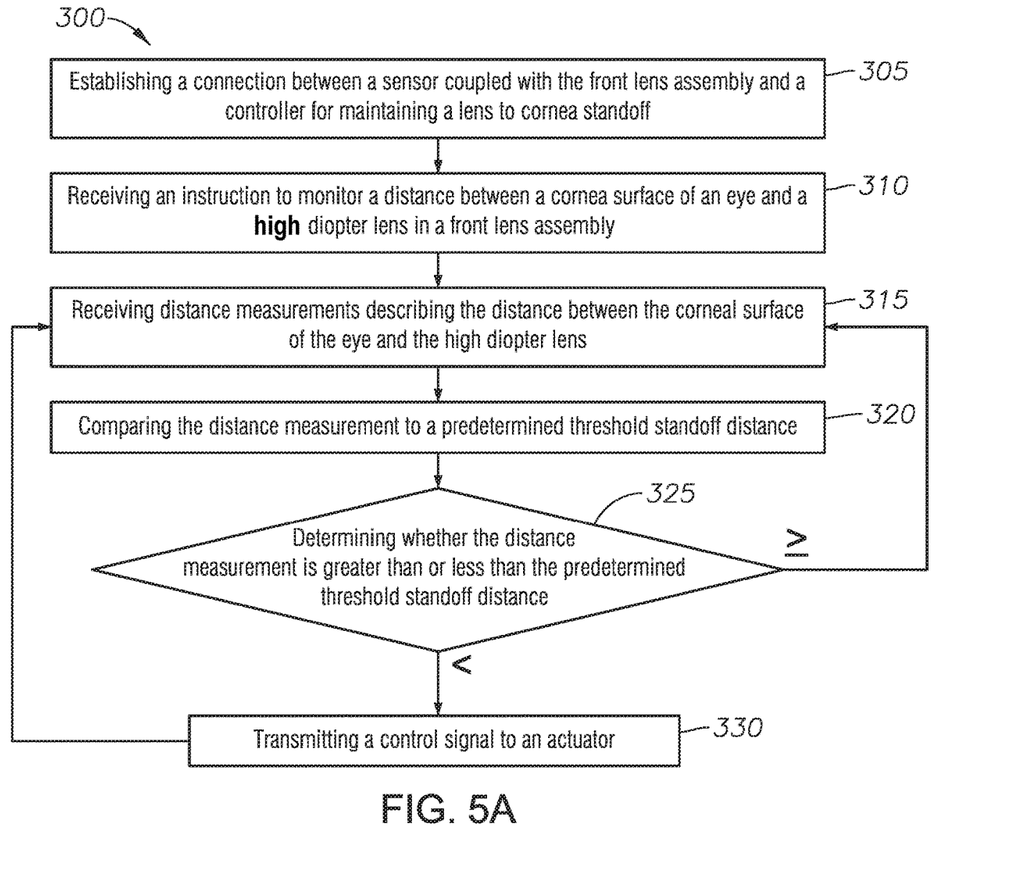
FIG. 5A illustrates a method for preventing a lens from getting too close to a cornea.

FIG. 5A illustrates a method 300 for preventing a lens from getting too close to a cornea in an ophthalmic microscope and front lens assembly system. The method 300 involves (at 305) establishing a connection between a sensor coupled with the front lens assembly and a controller for maintaining a lens to cornea standoff. As explained above, a sensor can be configured to detect the distance between a corneal surface of an eye and a high diopter lens in a front lens assembly and to transmit the detected distance to a controller. In some cases, establishing a connection between the sensor and the controller involves a wired connection in which distance detection information is transmitted from the sensor to the controller via the wired connection. In some cases, a wireless connection (e.g. a Bluetooth connection) is established between the sensor and the controller and the sensor is configured to wirelessly send distance detection information to the controller.

Next, the method 300 involves (at 310) receiving an instruction to monitor a distance between a corneal surface of an eye and a high diopter lens in a front lens assembly. In some cases, the ophthalmic microscope and front lens assembly system can include a user interface that is used to enter instructions. After surgical staff prepare the ophthalmic microscope and front lens assembly system and positions the high diopter lens under the lens arrangement and above a patient's eye, the user interface can be used to enter an instruction to begin monitoring the distance between a corneal surface of an eye and a high diopter lens.

After monitoring begins, the method 300 involves (at 315) receiving, from a sensor, distance measurements describing the distance between the corneal surface of the eye and the high diopter lens. Next, the method 300 involves at 320) comparing the distance measurement to a predetermined threshold standoff distance and (at 325) determining whether the distance measurement is greater than, equal to, or less than the predetermined threshold standoff distance.

When the distance measurement is greater than or equal to the predetermined threshold standoff distance, the method 300 involves (at 315) continuing to monitor the distance and receiving distance measurements describing the distance between the corneal surface of the eye and the high diopter lens. When the distance measurement is less than the predetermined threshold standoff distance, the method 300 involves (at 330) transmitting a control signal to an actuator; the control signal describes how to adjust the front lens assembly to position the high diopter lens at the predetermined threshold distance.

Figure 5B:
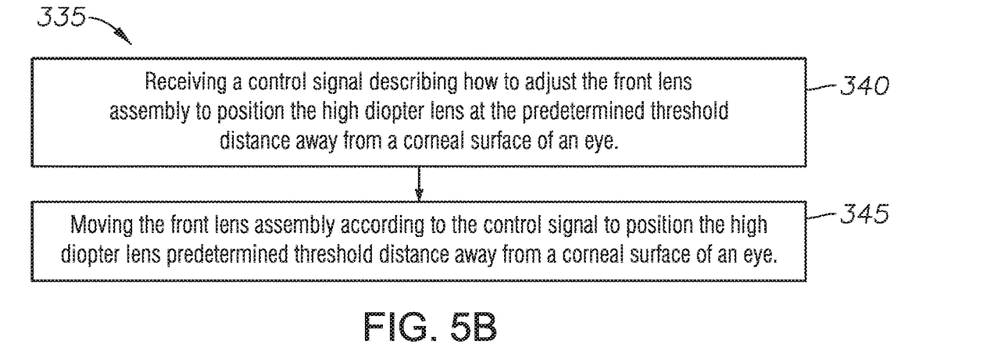
FIG. 5B illustrates a method of adjusting a front lens assembly to position a high diopter lens at the predetermined threshold distance away from a corneal surface of an eye.
Figure 5C:
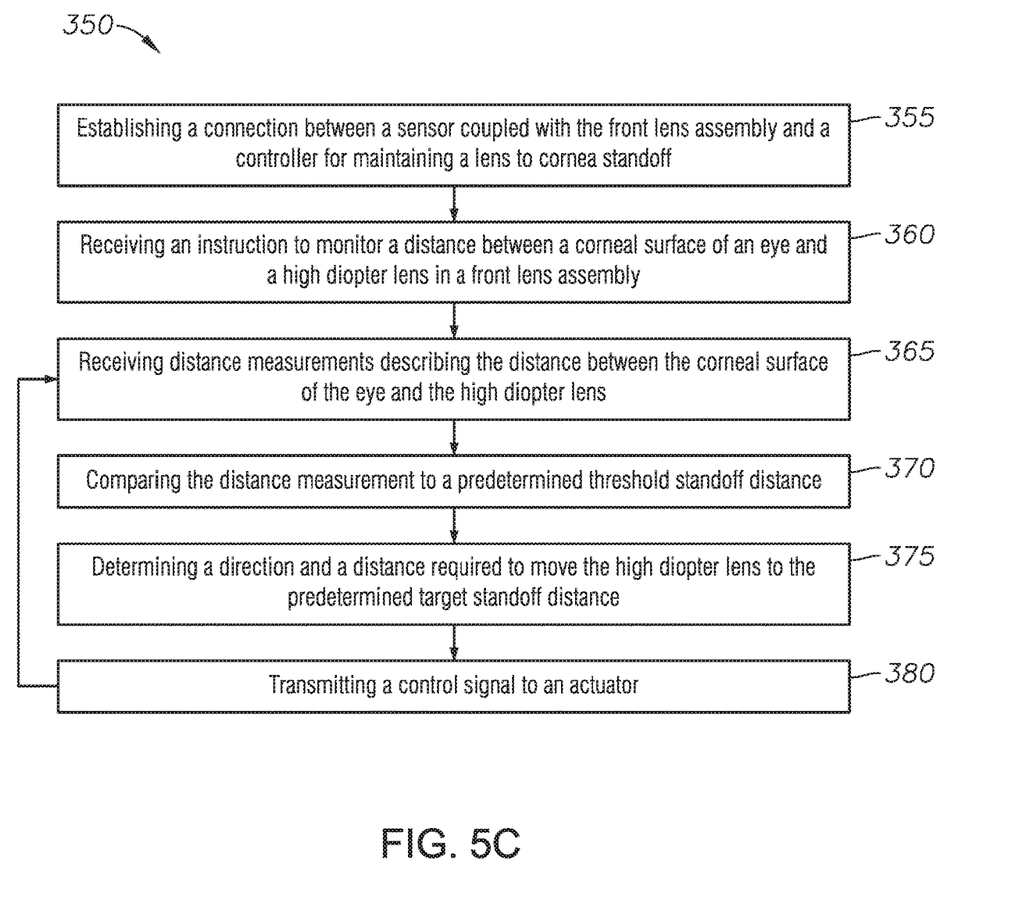
FIG. 5C illustrates a method for maintaining a target standoff distance between a high diopter lens and a cornea in an ophthalmic microscope and front lens assembly system.

While the disclosure describes adjusting the front lens assembly in response to determining that the distance between the high diopter lens and a surface of the eye is less than a threshold, those with ordinary skill in the art having the benefit of the present disclosure will readily appreciate that some other embodiments can involve distances greater than the same threshold, a separate threshold causing the actuator to re-position the front lens assembly, or a predetermined target standoff distance, as explained in greater detail in FIG. 5C below.

Also, the method 300 involves (at 315) continuing to monitor the distance and receiving distance measurements describing the distance between the corneal surface of the eye and the high diopter lens 315.

FIG. 5B illustrates a method 335 of adjusting a front lens assembly to position a high diopter lens at the predetermined threshold distance away from a corneal surface of an eye. The method 335 involves (at 340) receiving, by an actuator, a control signal describing how to adjust the front lens assembly to position the high diopter lens at the predetermined threshold distance away from a corneal surface of an eye. Next, the method involves (at 345) moving, by the actuator, the front lens assembly according to the control signal to position the high diopter lens predetermined threshold distance away from a corneal surface of an eye.

FIG. 5C illustrates a method 350 for maintaining a target standoff distance between a high diopter lens and a cornea in an ophthalmic microscope and front lens assembly system. The method 350 involves (at 355) establishing a connection between a sensor coupled with the front lens assembly and a controller for maintaining a lens to cornea standoff and (at 360) receiving an instruction to monitor a distance between a corneal surface of an eye and a high diopter lens in a front lens assembly. Next, the method 350 involves (at 365) receiving, from a sensor, distance measurements describing the distance between the corneal surface of the eye and the high diopter lens and (at 370) comparing the distance measurement to a predetermined target standoff distance. Based on the distance measurement and the predetermined target standoff distance, the method 350 involves (at 375) determining a direction and distance required to move the high diopter lens to the determined target standoff distance and (at 380) transmitting a control signal to an actuator 380 describing how to adjust the front lens assembly to position the high diopter lens at the predetermined target standoff distance.

Figure 6:
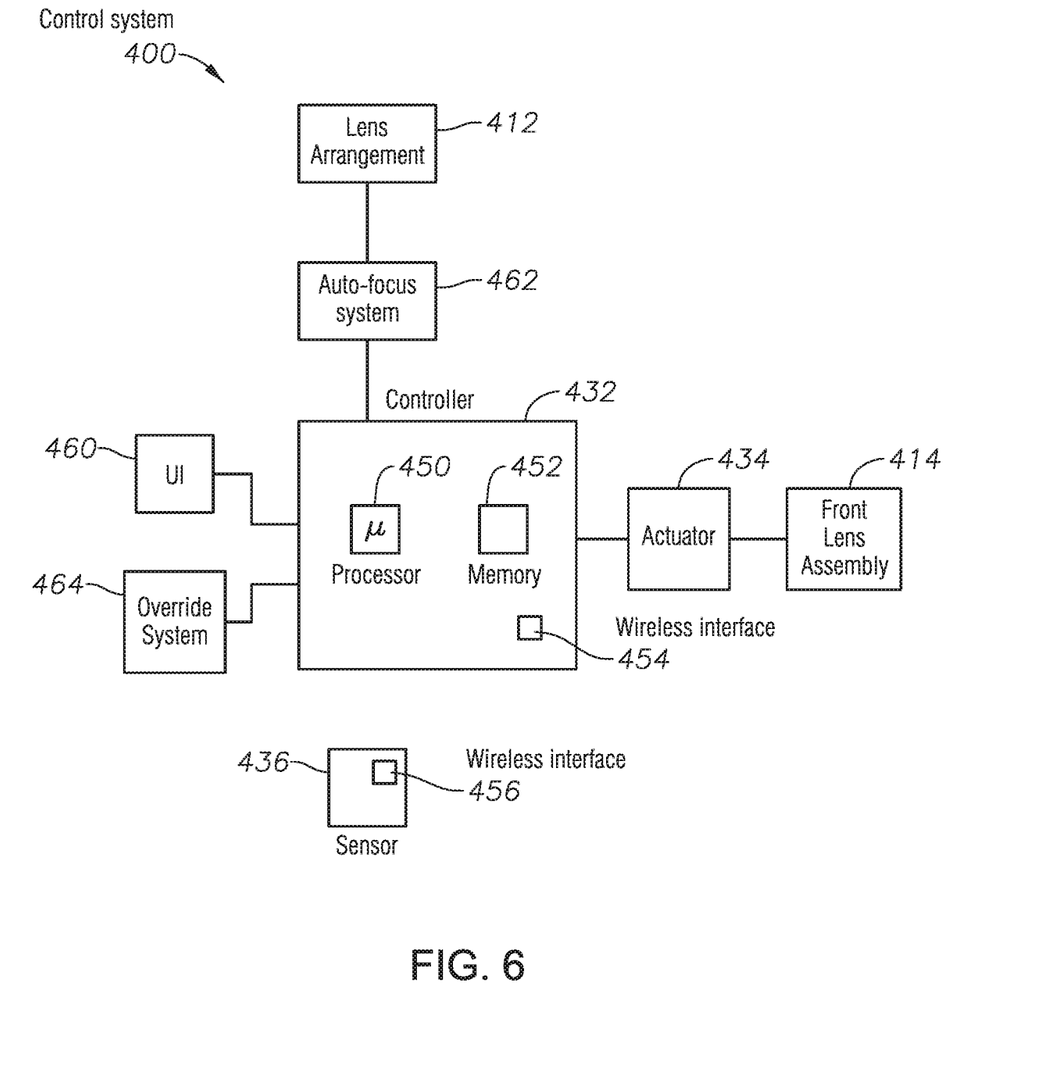
FIG. 6 illustrates a block diagram of a system used in an automatic lens to cornea standoff control system for maintaining a lens to cornea standoff.

As explained above, a controller used in an automatic lens to cornea standoff system can receive sensor data describing a distance between a high diopter lens and a surface of the eye and compare the distance to one or more predetermined threshold distances. FIG. 6 illustrates a block diagram of a system 400 used in an automatic lens to cornea standoff control system for maintaining a lens to cornea standoff.

The system 400 includes a controller 432 with a processor 450 and memory 452. The memory 452 can contain instructions which, when executed by the processor 450, cause the controller to perform the functions described in the present disclosure. The controller 432 can further include a wireless interface 454 for communicating with other components of the system 400. For example, in some cases, the controller 432 is wirelessly connected with a wireless interface 456 in a sensor 436 that detects the distance between a high diopter lens and a surface of an eye.

As explained above, the controller 432 can receive a distance measurement of the distance between a surface of the eye and the high diopter lens and the controller can compare the distance measurement to one or more predetermined threshold standoff distances. In some cases, predetermined threshold standoff distances are pre-programmed default values stored in the memory 452. Also, the predetermined threshold standoff distances can be user-defined and can be entered via a user interface 460 coupled with the controller 432. The user-interface 460 can be a stand-alone user interface. Also, the controller 432 can cause another device to display the user interface 460. For example, the controller 432 can be communicatively coupled with a surgical console specially designed for performing ophthalmic surgery and/or communicatively coupled with an ophthalmic microscope. In these cases, the user interface 460 can be a user interface native to the surgical console and/or ophthalmic microscope.

Whichever way the threshold standoff distances are defined, the controller 432 can compare the received distance measurement of the distance between a surface of the eye and the high diopter lens from the sensor 436 and compare the measurement with the threshold standoff distance. When a threshold is exceeded, the controller 432 can transmit, to an actuator 434, a control signal describing how to adjust a front lens assembly 414.

As explained above, adjustments made to a front lens assembly and, therefore, a position of a high diopter lens can affect an image being viewed through an ophthalmic microscope focused on the high diopter lens. So, the control system 400 can further include an auto-focus system 462 which can interpret the control signal sent to the actuator, determine how to re-focus a lens arrangement to maintain focus, and transmit an additional control signal to the lens arrangement 412 of the ophthalmic microscope. In some cases, the controller 432 and auto-focus system 462 are integral in a single module.

In some cases, a situation can dictate that adjusting the front lens assembly is not desirable. For example, during a critical point in a retinal surgery, a surgeon may not want to be distracted by a change in the position of the high diopter lens. Accordingly, the control system 400 can also include an over-ride system 464 which can prevent the controller from transmitting the control signal. In some cases, the over-ride system can include a manual over-ride switch (e.g. a foot brake). In some cases, the controller is configured to receive (e.g. from the user interface 460) surgical data such as surgical plan data, real-time surgical process data, etc. Based on the surgical data, the over-ride system 464 can determine points during the surgery where adjustments to the front lens assembly 414 and the high diopter lens would not be appropriate and the over-ride system 460 can prevent transmission of the control signal at those points.

Figure 7:
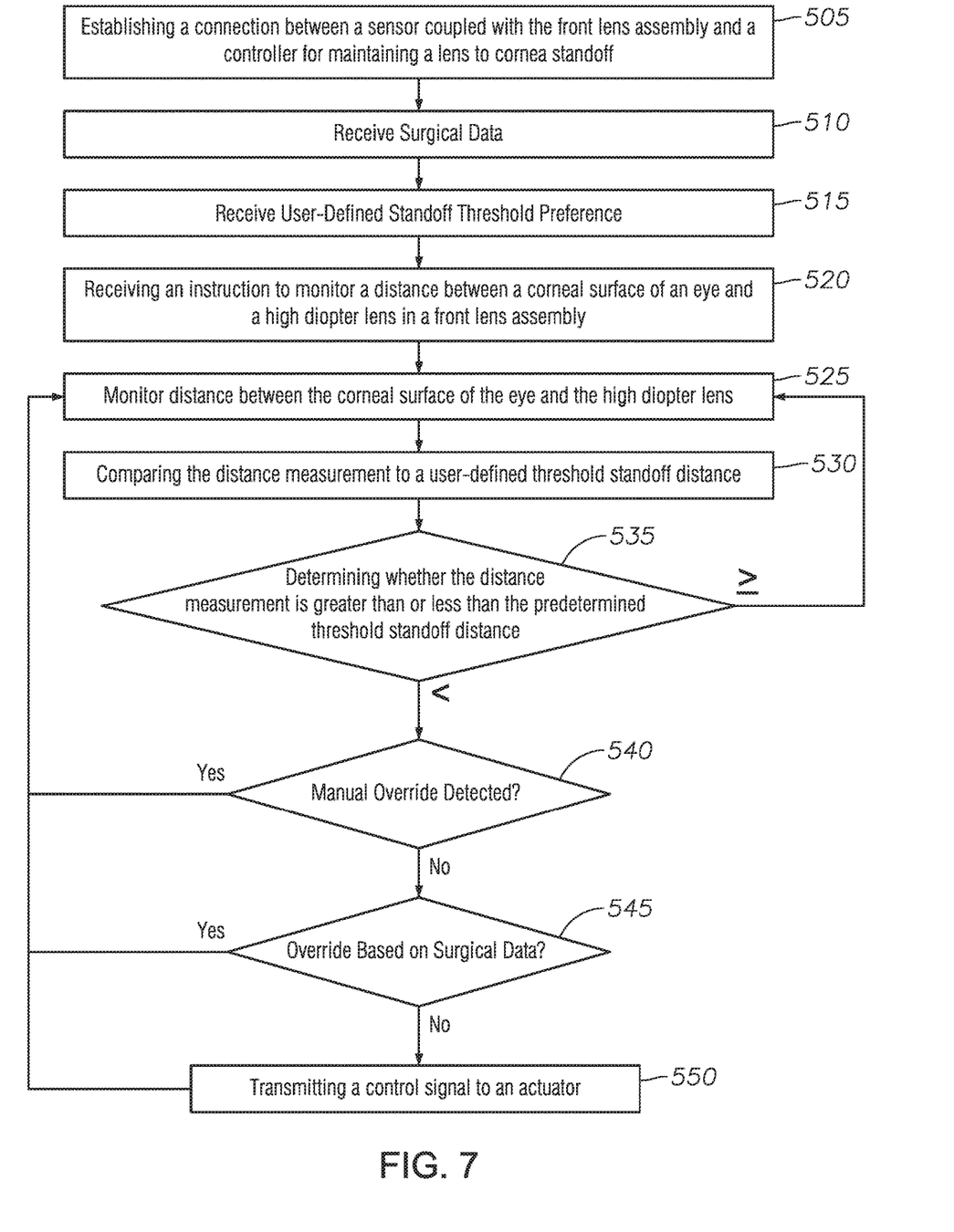
FIG. 7 illustrates a method for preventing contact between a lens and cornea in an ophthalmic microscope and front lens assembly system.

FIG. 7 illustrates a method for preventing contact between a lens and cornea in an ophthalmic microscope and front lens assembly system. The method involves (at 505) establishing a connection between a sensor coupled with the front lens assembly and a standoff controller for maintaining a lens to cornea standoff. In some cases, the standoff controller is communicatively connected to a surgical console configured to process pre-op surgical data and/or surgery plans and monitor planned surgical progress as well as actual real-time surgical progress. So, after a connection is made between the sensor and the controller, the method involves (at 510) the standoff controller receiving surgical data relating to over-riding automatic lens standoff adjustment. Similarly, the method involves fat 515) receiving (e.g. via a user interface on the surgical console) user-defined standoff threshold preference.

Once surgical staff is ready to begin using the high diopter lens, the method 500 can involve (at 520) receiving an instruction to monitor a distance between a corneal surface of an eye and a high diopter lens in a front lens assembly. After monitoring begins, the method 500 involves (at 525) receiving, from a sensor, distance measurements describing the distance between the corneal surface of the eye and the high diopter lens. Next, the method 500 involves (at 530) comparing the distance measurement to a predetermined threshold standoff distance and (at 535) determining whether the distance measurement is greater than, equal to, or less than the predetermined threshold standoff distance.

When the distance measurement is greater than or equal to the predetermined threshold standoff distance, the method 500 involves (at 525) continuing to monitor the distance and receiving distance measurements describing the distance between the corneal surface of the eye and the high diopter lens.

When the distance measurement is less and the predetermined threshold standoff distance, the method 500 involves (at 540) determining when a manual override command has been received from the surgical staff. When a manual override command has been received from the surgical staff, the method involves (at 525) continuing to monitor the distance and receiving distance measurements describing the distance between the corneal surface of the eye and the high diopter lens.

When a manual override command has not been received, the method 500 involves (at 545) determining when to override adjustment of the high diopter lens based on surgical data.

When surgical data dictates overriding high diopter lens adjustment, the method involves (at 525) continuing to monitor the distance and receiving distance measurements describing the distance between the corneal surface of the eye and the high diopter lens 515. Alternatively, when an override based on surgical data has not been received, the method 500 involves (at 550) transmitting a control signal to an actuator; the control signal describing how to adjust the front lens assembly to position the high diopter lens at the predetermined threshold distance.

Figure 8A:
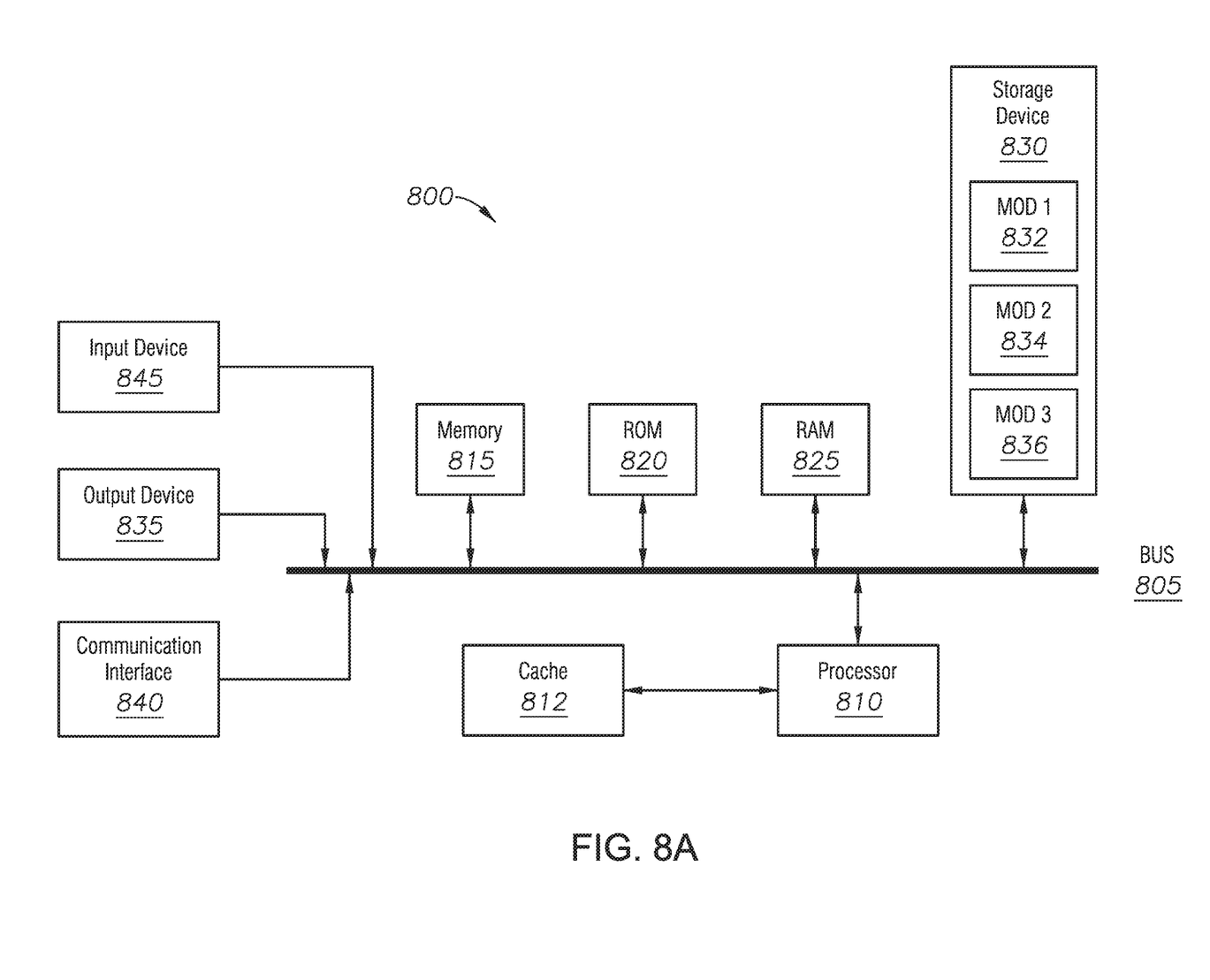
FIG. 8A and FIG. 8B illustrate exemplary possible system embodiments.
Figure 8B:
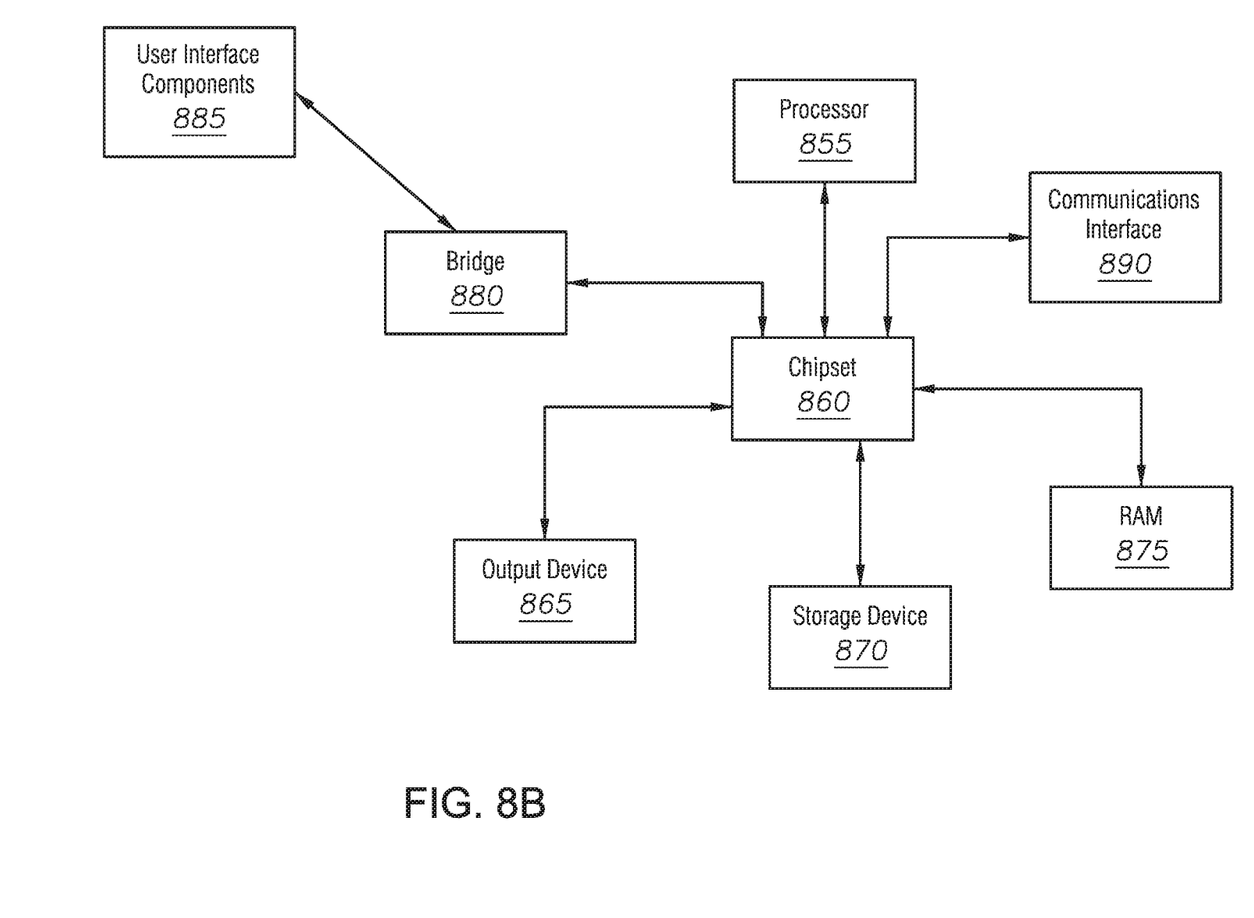

FIG. 8A and FIG. 8B illustrate exemplary possible system embodiments. The more appropriate embodiment will be apparent to those of ordinary skill in the art when practicing the present technology. Persons of ordinary skill in the art will also readily appreciate that other system embodiments are possible.

FIG. 8A illustrates a conventional system bus computing system architecture 800 wherein the components of the system are in electrical communication with each other using a bus 805. Exemplary system 800 includes a processing unit (CPU or processor) 810 and a system bus 805 that couples various system components including the system memory 815, such as read only memory (ROM) 820 and random access memory (RAM) 825, to the processor 810. The system 800 can include a cache of high-speed memory connected directly with, in close proximity to, or integrated as part of the processor 810. The system 800 can copy data from the memory 815 and/or the storage device 830 to the cache 812 for quick access by the processor 810. In this way, the cache can provide a performance boost that avoids processor 810 delays while waiting for data. These and other modules can control or be configured to control the processor 810 to perform various actions. Other system memory 815 may be available for use as well. The memory 815 can include multiple different types of memory with different performance characteristics. The processor 810 can include any general purpose processor and a hardware module or software module, such as module 1 832, module 2 834, and module 3 836 stored in storage device 830, configured to control the processor 810 as well as a special-purpose processor where software instructions are incorporated into the actual processor design. The processor 810 may essentially be a completely self-contained computing system, containing multiple cores or processors, a bus, memory controller, cache, etc. A multi-core processor may be symmetric or asymmetric.

To enable user interaction with the computing device, an input device 845 can represent any number of input mechanisms, such as a microphone for speech, a touch-sensitive screen for gesture or graphical input, keyboard, mouse, motion input, speech and so forth. An output device 835 can also be one or more of a number of output mechanisms known to those of skill in the art. In some instances, multimodal systems can enable a user to provide multiple types of input to communicate with the computing device 800. The communications interface 840 can generally govern and manage the user input and system output. There is no restriction on operating Off any particular hardware arrangement and therefore the basic features here may easily be substituted for improved hardware or firmware arrangements as they are developed.

Storage device 830 is a non-volatile memory and can be a hard disk or other types of computer readable media which can store data that are accessible by a computer, such as magnetic cassettes, flash memory cards, solid state memory devices, digital versatile disks, cartridges, random access memories (RAMs) 825, read only memory (ROM) 820, and hybrids thereof.

The storage device 830 can include software modules 832, 834, 836 for controlling the processor 810. Other hardware or software modules are contemplated. The storage device 830 can be connected to the system bus 805. In one aspect, a hardware module that performs a particular function can include the software component stored in a computer-readable medium in connection with the necessary hardware components, such as the processor 810, bus 805, display 835, and so forth, to carry out the function.

FIG. 8B illustrates a computer system having a chipset architecture that can be used in executing the described method and generating and displaying a graphical user interface (GUI). Computer system is an example of computer hardware, software, and firmware that can be used to implement the disclosed technology. System can include a processor 855, representative of any number of physically and/or logically distinct resources capable of executing software, firmware, and hardware configured to perform identified computations. Processor 855 can communicate with a chipset 860 that can control input to and output from processor 855. In this example, chipset 860 outputs information to output 865, such as a display, and can read and write information to storage device 870, which can include magnetic media, and solid state media, for example. Chipset 860 can also read data from and write data to RAM 875. A bridge 880 for interfacing with a variety of user interface components 885 can be provided for interfacing with chipset 860. Such user interface components 885 can include a keyboard, a microphone, touch detection and processing circuitry, a pointing device, such as a mouse, and so on. In general, inputs to system can come from any of a variety of sources, machine generated and/or human generated.

Chipset 860 can also interface with one or more communication interfaces 890 that can have different physical interfaces. Such communication interfaces can include interfaces for wired and wireless local area networks, for broadband wireless networks, as well as personal area networks. Some applications of the methods for generating, displaying, and using the GUI disclosed herein can include receiving ordered datasets over the physical interface or be generated by the machine itself by processor 855 analyzing data stored in storage 870 or 875. Further, the machine can receive inputs from a user via user interface components 885 and execute appropriate functions, such as browsing functions by interpreting these inputs using processor 855.

It can be appreciated that exemplary systems 800 and 850 can have more than one processor 810 or be part of a group or cluster of computing devices networked together to provide greater processing capability.

For clarity of explanation, in some instances the present technology may be presented as including individual functional blocks including functional blocks comprising devices, device components, steps or routines in a method embodied in software, or combinations of hardware and software.

In some embodiments the computer-readable storage devices, mediums, and memories can include a cable or wireless signal containing a bit stream and the like. However, when mentioned, non-transitory computer-readable storage media expressly exclude media such as energy, carrier signals, electromagnetic waves, and signals per se.

Methods according to the above-described examples can be implemented using computer-executable instructions that are stored or otherwise available from computer readable media. Such instructions can comprise, for example, instructions and data which cause or otherwise configure a general purpose computer, special purpose computer, or special purpose processing device to perform a certain function or group of functions. Portions of computer resources used can be accessible over a network. The computer executable instructions may be, for example, binaries, intermediate format instructions such as assembly language, firmware, or source code. Examples of computer-readable media that may be used to store instructions, information used, and/or information created during methods according to described examples include magnetic or optical disks, flash memory, USB devices provided with non-volatile memory, networked storage devices, and so on.

Devices implementing methods according to these disclosures can comprise hardware, firmware and/or software, and can take any of a variety of form factors. Typical examples of such form factors include laptops, smart phones, small form factor personal computers, personal digital assistants, and so on. Functionality described herein also can be embodied in peripherals or add-in cards. Such functionality can also be implemented on a circuit board among different chips or different processes executing in a single device, by way of further example.

The instructions, media for conveying such instructions, computing resources for executing them, and other structures for supporting such computing resources are means for providing the functions described in these disclosures.

The above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

What is claimed is:

1. An automatic lens to cornea standoff control system comprising:
    an ophthalmic microscope with a lens arrangement configured for viewing images of an eye;
    a front lens assembly having a lens holder containing a high diopter lens, wherein the front lens assembly is configured to adjustably position the high diopter lens between the lens arrangement of the ophthalmic microscope and the eye;
    a user interface for receiving a user-defined predetermined threshold standoff distance;
    a sensor configured to detect a distance between the high diopter lens and a surface of the eye and to transmit a detected distance;
    a controller configured to receive the detected distance from the sensor, determine if the detected distance is less than the user-defined predetermined threshold standoff distance, and, unless an over-ride signal has been received from an over-ride control system, transmit a control signal to cause the high diopter lens to move away from the surface of the eye; and
    an actuator coupled with the front lens assembly, the actuator configured to receive the control signal and cause the high diopter lens to move to the user-defined predetermined threshold standoff distance away from the surface of the eye.

2. The automatic lens to cornea standoff control system of claim 1, wherein the front lens assembly comprises a multi-sectional articulating arm, and wherein the actuator is configured to cause a plurality of sections of the multi-sectional articulating arm to articulate and cause the high diopter lens to move the distance away from the surface of the eye while keeping the high diopter lens in a beampath of the lens arrangement.

3. The automatic lens to cornea standoff control system of claim 1, further comprising:
    an auto-focus system coupled with the controller and the lens arrangement of the ophthalmic microscope, wherein the auto-focus system is configured to automatically focus the lens arrangement to resolve an image of the eye that was being resolved before a position of the high diopter lens was moved according to the control signal.

4. The automatic lens to cornea standoff control system of claim 1, wherein the front lens assembly comprises a screw drive system for adjustably positioning the lens holder between the lens arrangement of the ophthalmic microscope and the eye.

5. The automatic lens to cornea standoff control system of claim 1, wherein the sensor is coupled with the lens holder of the front lens assembly.

6. The automatic lens to cornea standoff control system of claim 1, wherein the sensor is selected from among a group of sensors consisting of an ultrasonic sensor, a laser triangulation sensor, and an infrared sensor.

7. The automatic lens to cornea standoff control system of claim 1, wherein the controller includes the over-ride control system configured to receive the over-ride signal and prevent the controller from transmitting the control signal.

8. The automatic lens to cornea standoff control system of claim 7, wherein the controller is configured to receive surgical data, determine when, based on the surgical data, during a surgery adjustments would not be appropriate, and wherein the controller is further configured to generate the over-ride signal based on that determination.

9. The automatic lens to cornea standoff control system of claim 1, wherein the sensor includes a wireless transducer configured to transmit the detected distance, wherein the controller includes a wireless transceiver for receiving the detected distance and transmitting the control signal, and wherein the actuator includes a wireless receiver for receiving the control signal.

10. A method of maintaining a lens to cornea standoff comprising:
   receiving an instruction to monitor a distance between a corneal surface of an eye and a high diopter lens in a front lens assembly positioned between a lens arrangement of an ophthalmic microscope and the corneal surface of an eye;
   receiving, from a user interface, a user-defined predetermined threshold standoff distance;
   receiving, from a sensor, a distance measurement of the distance between the corneal surface of the eye and the high diopter lens;
   comparing the distance measurement to the user-defined predetermined threshold standoff distance to detect if the distance measurement is less than the user-defined predetermined threshold standoff distance;
   if an over-ride signal has not been received from an over-ride control system, transmitting a control signal to an actuator if the distance measurement is less than the user-defined predetermined threshold standoff distance, wherein the control signal causes the high diopter lens to be positioned at the user-defined predetermined threshold distance; and
   if an over-ride signal has been received from the over-ride control system, not transmitting the control signal to the actuator.

11. The method of maintaining a lens to cornea standoff of claim 10, wherein if an over-ride signal has not been received, the method further comprises:
   receiving, by the actuator, the control signal; and
   moving, by the actuator, the front lens assembly according to the control signal to position the high diopter lens at the user-defined predetermined threshold distance.

12. The method of maintaining a lens to cornea standoff of claim 10, further comprising:
   transmitting, to an autofocus system coupled with the lens arrangement of the ophthalmic microscope, an instruction for focusing the lens arrangement to resolve an image of the eye that was being resolved before a position of the high diopter lens was moved according to the control signal.

13. The method of maintaining a lens to cornea standoff of claim 10, wherein if an over-ride signal has been received from the over-ride control system, the method further comprises:
   throttling the transmission of the control signal.

14. The method of claim 10, further comprising receiving surgical data, determining when, based on the surgical data, during a surgery where adjustments would not be appropriate, and generating the over-ride signal based on that determination.

15. The method of claim 10, wherein the user-defined predetermined threshold standoff distance is a number entered by a user into the user interface.

16. The method of claim 10, further comprising the over-ride control system processing pre-op surgical data and monitoring actual real-time surgical progress to determine when to generate the over-ride signal.

17. A non-transitory computer-readable medium storing instructions that are executable by one or more computer processors of a computing device to:
   receive an instruction to monitor a distance between a corneal surface of an eye and a high diopter lens in a front lens assembly positioned between a lens arrangement of an ophthalmic microscope and the corneal surface of an eye;
   receive, from a user interface, a user-defined predetermined threshold standoff distance;
   receive, from a sensor, a distance measurement of the distance between the corneal surface of the eye and the high diopter lens;
   compare the distance measurement to the user-defined predetermined threshold standoff distance to detect if the distance measurement is less than the user-defined predetermined threshold standoff distance;
   if an over-ride signal has not been received from an over-ride control system, transmit a control signal to an actuator if the distance measurement is less than the user-defined predetermined threshold standoff distance, wherein the control signal causes the high diopter lens to be positioned at the user-defined predetermined threshold distance; and
   if an over-ride signal has been received from the over-ride control system, not transmitting the control signal to the actuator.

18. The non-transitory computer-readable medium of claim 17 further storing instructions that are executable by one or more computer processors of the computing device to, if an over-ride signal has not been received from an over-ride control system:
   receive the control signal; and
   cause the actuator to move the front lens assembly according to the control signal to position the high diopter lens at the user-defined predetermined threshold distance.

19. The non-transitory computer-readable medium of claim 17 further storing instructions that are executable by one or more computer processors of the computing device to:
   transmit, to an autofocus system coupled with the lens arrangement of the ophthalmic microscope, an instruction for focusing the lens arrangement to resolve an image of the eye that was being resolved before a position of the high diopter lens was moved according to the control signal.

20. The non-transitory computer-readable medium of claim 17 further storing instructions that are executable by one or more computer processors of the computing device to: receive surgical data, determine when, based on the surgical data, during a surgery where adjustments would not be appropriate, and generate the over-ride signal based on that determination.

* * * * *